United States Patent [19]

Pfahl

[11] Patent Number: 5,144,007

[45] Date of Patent: Sep. 1, 1992

[54] THYROID HORMONE RECEPTOR

[75] Inventor: Magnus Pfahl, Solana Beach, Calif.

[73] Assignee: La Jolla Cancer Research Foundation, La Jolla, Calif.

[21] Appl. No.: 604,334

[22] Filed: Oct. 24, 1990

Related U.S. Application Data

[63] Continuation of Ser. No. 266,529, Nov. 3, 1988, abandoned.

[51] Int. Cl.$^5$ .................... C07K 13/00; C07K 15/28
[52] U.S. Cl. ................... 530/350; 530/387.9; 530/395; 530/388.22; 530/389.1; 435/69.1; 536/27
[58] Field of Search ............ 530/350, 395, 387; 435/69.1; 536/27

[56] References Cited

PUBLICATIONS

Ichikawa et al. Chem. Abstracts 105:91787n, Sep. 15, 1986.
Sap et al. Nature 324:635–640, Dec. 18, 1986.
Benbrook et al. Science 238:788–791 Nov. 6, 1987.
Spurr et al. EMBO Journal 3(1) pp. 159–163, 1984.
Hudson & Hay "Practical Immunology" Blackwell Press pp. 303–326 (1980).
Davis et al. "Microbiology" Harper & Row, Publishers pp. 338–341.
Weinberger et al., The c-erg-A gene encodes a thyroid hormone receptor, Nature 324:641–646 (1986).
Thompson et al., Identification of a Novel Thyroid Hormone Receptor Expressed in the Mammalian Central Nervous System, Science 237:1610–1613 (1987).

*Primary Examiner*—David L. Lacey
*Assistant Examiner*—Nina Ossanna
*Attorney, Agent, or Firm*—Needle & Rosenberg

[57] ABSTRACT

This invention provides a substantially purified thyroid hormone receptor, termed herbA-T, defined by its complete amino acid sequence deduced from its cDNA and the binding of thyroid hormone by the protein translated from the mRNA corresponding to the cDNA. The cDNA, the protein produced from it, and antibodies reactive therewith are also provided.

4 Claims, 9 Drawing Sheets

```
              10        20        30        40        50        60
    CGCGTCGCTGCCCAGCCCGGTCCGGCGCGCCACGCAGTGGATCTCTGGACAGGACAAGAC 70        80        90       100       110       120
    TCCGAAGCTACTCCCCCAGCACACAGCCCGGGACCCACAAACCCAGCTTGCCCCCAGCCC 130       140       150       160       170       180
    TCCCACCTGCCACTCCCTGGCCCCTCCCACCGGCCGCCCCCCTTGGCGCGGGCGCATGGT 190       200       210       220       230       240
    GTGAAAGGCCAAGTGCTGAGGCGGGTATCATGGGTGCTGTGCCCTAGGCCTGGGTGGCAG 250       260       270       280       290       300
    GGGGTGGGTGGCCTGTGGGTGTGCCGGGGGGCCAGTGTGCCCACCCCAGTCTCTTGGCG 310       320       330       340       350       360
    TGCTGGAGGGCATCCTGGATGGAATTGAAGTGAATGGAACAGAAGCCAAGCAAGGTGGAG
                                          MetGluGlnLysProSerLysValGlu 370       380       390       400       410       420
    TGTGGGTCAGACCCAGAGGAGAACAGTGCCAGGTCACCAGATGGAAAGCGAAAAAGAAAG
    CysGlySerAspProGluGluAsnSerAlaArgSerProAspGlyLysArgLysArgLys 430       440       450       460       470       480
    AACGGCCAATGTTCCCTGAAAAGCAGCATGTCAGGGTATATCCCTAGTTACCTGGACAAA
    AsnGlyGlnCysSerLeuLysSerSerMetSerGlyTyrIleProSerTyrLeuAspLys 490       500       510       520       530       540
    GACGAGCAGTGTGTCGTGTGTGGGGACAAGGCAACTGGTTATCACTACCGCTGTATCACT
    AspGluGlnCysValValCysGlyAspLysAlaThrGlyTyrHisTyrArgCysIleThr 550       560       570       580       590       600
    TGTGAGGGCTGCAAGGGCTTCTTTCGCCGCACAATCCAGAAGAACCTCCATCCCACCTAT
    CysGluGlyCysLysGlyPhePheArgArgThrIleGlnLysAsnLeuHisProThrTyr
```

FIG.1A

```
     610       620       630       640       650       660
TCCTGCAAATATGACAGCTGCTGTGTCATTGACAAGATCACCCGCAATCAGTGCCAGCTG
SerCysLysTyrAspSerCysCysValIleAspLysIleThrArgAsnGlnCysGlnLeu 670       680       690       700       710       720
TGCCGCTTCAAGAAGTGCATCGCCGTGGCCATGGCCATGGACTTGGTTCTAGATGACTCG
CysArgPheLysLysCysIleAlaValAlaMetAlaMetAspLeuValLeuAspAspSer 730       740       750       760       770       780
AAGCGGGTGGCCAAGCGTAAGCTGATTGAGCAGAACCGGGAGCGGCGGCGGAAGGAGGAG
LysArgValAlaLysArgLysLeuIleGluGlnAsnArgGluArgArgArgLysGluGlu 790       800       810       820       830       840
ATGATCCGATCACTGCAGCAGCGACCAGAGCCCACTCCTGAAGAGTGGGATCTGATCCAC
MetIleArgSerLeuGlnGlnArgProGluProThrProGluGluTrpAspLeuIleHis 850       860       870       880       890       900
ATTGCCACAGAGGCCCATCGCAGCACCAATGCCCAGGGCAGCCATTGGAAACAGAGGCGG
IleAlaThrGluAlaHisArgSerThrAsnAlaGlnGlySerHisTrpLysGlnArgArg 910       920       930       940       950       960
AAATTCCTGCCCGATGACATTGGCCAGTCACCCATTGTCTCCATGCCGGACGGAGACAAG
LysPheLeuProAspAspIleGlyGlnSerProIleValSerMetProAspGlyAspLys 970       980       990      1000      1010      1020
GTGGACCTGGAAGCCTTCAGCGAGTTTACCAAGATCATCACCCCGGCCATCACCCGTGTG
ValAspLeuGluAlaPheSerGluPheThrLysIleIleThrProAlaIleThrArgVal 1030      1040      1050      1060      1070      1080
GTGGACTTTGCCAAAAAACTGCCCATGTTCTCCGAGCTGCCTTGCGAAGACCAGATCATC
ValAspPheAlaLysLysLeuProMetPheSerGluLeuProCysGluAspGlnIleIle 1090      1100      1110      1120      1130      1140
CTCCTGAAGGGGTGCTGCATGGAGATCATGTCCCTGCGGGCGGCTGTCCGCTACGACCCT
LeuLeuLysGlyCysCysMetGluIleMetSerLeuArgAlaAlaValArgTyrAspPro 1150      1160      1170      1180      1190      1200
GAGAGCGACACCCTGACGCTGAGTGGGGAGATGGCTGTCAAGCGGGAGCAGCTCAAGAAT
GluSerAspThrLeuThrLeuSerGlyGluMetAlaValLysArgGluGlnLeuLysAsn
```

FIG.1B

```
      1210      1220      1230      1240      1250      1260
GGCGGCCTGGGCGTAGTCTCCGACGCCATCTTCGAACTGGGCAAGTCACTCTCTGCCTTT
GlyGlyLeuGlyValValSerAspAlaIlePheGluLeuGlyLysSerLeuSerAlaPhe 1270      1280      1290      1300      1310      1320
AACCTGGATGACACGGAAGTGGCTCTGCTGCAGGCTGTGCTGCTAATGTCAACAGACCGC
AsnLeuAspAspThrGluValAlaLeuLeuGlnAlaValLeuLeuMetSerThrAspArg 1330      1340      1350      1360      1370      1380
TCGGGCCTGCTGTGTGTGGACAAGATCGAGAAGAGTCAGGAGGCGTACCTGCTGGCGTTC
SerGlyLeuLeuCysValAspLysIleGluLysSerGlnGluAlaTyrLeuLeuAlaPhe 1390      1400      1410      1420      1430      1440
GAGCACTACGTCAACCACCGCAAACACAACATTCCGCACTTCTGGCCCAAGCTGCTGATG
GluHisTyrValAsnHisArgLysHisAsnIleProHisPheTrpProLysLeuLeuMet 1450      1460      1470      1480      1490      1500
AAGGAGAGAGAAGTGCAGAGTTCGATTCTGTACAAGGGGGCAGCGGCAGAAGGCCGGCCG
LysGluArgGluValGlnSerSerIleLeuTyrLysGlyAlaAlaAlaGluGlyArgPro 1510      1520      1530      1540      1550      1560
GGCGGGTCACTGGGCGTCCACCCGGAAGGACAGCAGCTTCTCGGAATGCATGTTGTTCAG
GlyGlySerLeuGlyValHisProGluGlyGlnGlnLeuLeuGlyMetHisValValGln 1570      1580      1590      1600      1610      1620
GGTCCGCAGGTCCGGCAGCTTGAGCAGCAGCTTGGTGAAGCGGGAAGTCTCCAAGGGCCG
GlyProGlnValArgGlnLeuGluGlnGlnLeuGlyGluAlaGlySerLeuGlnGlyPro 1630      1640      1650      1660      1670      1680
GTTCTTCAGCACCAGAGCCCGAAGAGCCCGCAGCAGCGTCTCCTGGAGCTGCTCCACCGA
ValLeuGlnHisGlnSerProLysSerProGlnGlnArgLeuLeuGluLeuLeuHisArg 1690      1700      1710      1720      1730      1740
AGCGGAATTCTCCATGCCCGAGCGGTCTGTGGGGAAGACGACAGCAGTGAGGCGGACTCC
SerGlyIleLeuHisAlaArgAlaValCysGlyGluAspAspSerSerGluAlaAspSer 1750      1760      1770      1780      1790      1800
CCGAGCTCCTCTGAGGAGGAACCGGAGGTCTGCGAGGACCTGGCAGGCAATGCAGCCTCT
ProSerSerSerGluGluGluProGluValCysGluAspLeuAlaGlyAsnAlaAlaSer
```

FIG.1C

```
     1810      1820      1830      1840      1850      1860
CCCTGAAGCCCCCCAGAAGGCCGATGGGGAAGGAGAAGGAGTGCCATACCTTCTCCCAGG
Pro 1870      1880      1890      1900      1910      1920
CCTCTGCCCCAAGAGCAGGAGGTGCCTGAAAGCTGGGAGCGTGGGCTCAGCAGGGCTGGT 1930      1940      1950      1960      1970      1980
CACCTCCCATCCCGTAAGACCACCTTCCCTTCCTCAGCAGCCAAACATGGCCAGACTCCC 1990      2000      2010      2020      2030      2040
TTGCTTTTTGCTGTGTAGTTCCCTCTGCCTGGGATGCCCTTCCCCCTTTCTCTGCCTGGC 2050      2060      2070      2080      2090      2100
AACATCTTACTTGTCCTTTGAGGCCCCAACTCAAGTGTCACCTCCTTCCCCAGCTCCCCC
AGGCAGAAATAG

| | | | | | | | | | | | | | | | | | | | | | | | | |
|---|---|---|---|---|---|---|---|---|---|---|---|---|---|---|---|---|---|---|---|---|---|---|---|---|
| 1 | - | - | - | - | - | - | - | - | - | - | - | - | E | D | T | - | W | L | - | - | - | - | H | - | v-erbA |
| 1 | M | E | Q | K | P | S | K | V | E | C | G | S | D | P | E | E | - | W | L | - | - | - | - | - | cc-erbA |
| | | T | L | D | P | L | - | E | - | - | - | - | - | D | T | - | W | L | - | - | - | I | - | | hc-erbA-T |
| 50 | S | P | H | L | I | E | T | T | W | T | S | - | I | F | H | L | D | H | D | D | V | N | - | Q | hc-erbA-β |

(Sequence alignment figure — v-erbA, cc-erbA, hc-erbA-T, hc-erbA-β)

FIG.2A

```
185 N A - - L - - - - - - - - - - - L - - - - - - - - - - R - - N - - - -    v-erbA
199 M A - - - - - - - - - - - - - - - - - - - - - - - - - - - - - - - -    c-erbA
201 I V S M P D G D K V D L E A F S E F T K I I T P A I T R V V D F A K K L P M F S  hc-erbA-T
250 - N A - - E - G - - - - - - - H - - - - - - - - - - - - - - - - - C    hc-erbA-β

225 - - - - - - - - - - - - - - - - - - - - - - - - - - - - - - M - -    v-erbA
239 - - - - - - - - - - - - - - - - - - - - - - - - - - - - - - - - -    c-erbA
241 E L P C E D Q I I L L K G C C M E I M S L R A A V R Y D P E S D T L T L S G E M  hc-erbA-T
290 - - L - - - - - - - - - - - - - - - - - - - - - - - - - - - - N -    hc-erbA-β

265 - - - - - - - - - - - - - - - - - - D - - - - - - - - - - - Q -    v-erbA
279 - - - - - - - - - - - - - - - - - - D - - - - - - - - - - - - -    c-erbA
281 A V K R E Q L K N G G L G V V S D A I F E L G K S L S A F N L D D T E V A L L Q  hc-erbA-T
330 - I - - - - - - - - - - - - - - - - D - - - M - S - - - - - - - -    hc-erbA-β

305 - - - - - - - S - - T - - I - - - H - - - - - C - - S - - - Y - -    v-erbA
319 - - - - - - - S - - T - - I - - - - - - - - - C - - T - - - Y - -    c-erbA
321 A V L L M S T D R S G L L C V D K I E K S Q E A Y L L A F E H Y V N H R K H N I  hc-erbA-T
370 - I - - - - - S - - P - - A - - E R - - Y - D S F - - - - - - - H V  hc-erbA-β

345 - - - - - S - - - - - - - - - - - - - - - - - - - - - - -    v-erbA  ──── 44 residues
359 - - - - - - - - - - - - - - - - - - - - - - - - - - - - -    c-erbA  ──── 40 residues
361 P H F W P K L L M K                                         hc-erbA-T ──── 120 residues
410 T - - - - - - - - -                                         hc-erbA-β ──── 37 residues
```

THYROID HORMONE RECEPTOR

This application is a continuation of application Ser. No. 07/266,529, filed Nov. 3, 1988, now abandoned.

BACKGROUND OF THE INVENTION

The thyroid gland plays a vital role in controlling metabolic processes of the body. Under the control of the pituitary gland, it exerts its effects on various organs through the thyroid hormone. This hormone exists in two forms: 3,5,3'- triiodo - L - tyrosine ($T_3$) and 3,5,3',5-tetraiodo - L - tyrosine ($T_4$). Of these, $T_3$ is more active as a hormone, but both function in a similar fashion to regulate cellular functions.

Most tissues have an absolute requirement for thyroid hormone for proper function and grave, potentially lethal, diseases result from both too low and too high thyroid hormone activity. Recent discoveries have provided new tools for the assessment of such diseases. While it has been known that the thyroid hormone exerts its effects on cells through receptors, the precise nature of the receptors has until recently, been unknown.

The cDNAs of a human thyroid receptor and a chicken thyroid receptor (erbA) have now been cloned and their amino acid sequences and the general structure of the receptors deduced from them shown to be related to those of previously known steroid hormone receptors. (Sap et al., Nature 324:635 (1986); Weinberger et al., Nature 324:641 (1986), both of which are incorporated herein by reference.) The steroid hormone receptors include those for glucorcorticoids (Miesfield et al., Cell 46:389 (1986); Danielsen et al., EMBO J. 5:2513 (1986), both of which are incorporated herein by reference) and estrogen (Kumar et al., EMBO J. 5:2231 (1986), which is incorporated herein by reference). It has been generally thought that there was only one thyroid receptor. Should others exist, their identification would be of importance in assessing thyroid function.

There thus exists a need to clone and identify other human erbA genes which may include further receptors binding the thyroid hormones in order to be able to accurately assess the functioning of the thyroid system in patients. The present invention satisfies these needs and provides related advantages as well.

SUMMARY OF THE INVENTION

This invention relates to a substantially purified human thyroid hormone receptor, termed herbA-T or $hTR_\alpha$, defined by its complete amino acid sequence deduced from its cDNA and the binding of thyroid hormone by the protein translated from the mRNA corresponding to the cDNA.

The nucleic acids encoding herbA-T, the recombinant protein produced therefrom, and antibodies reactive therewith are useful for assessing of the presence of the receptor in tissues. Such assessments will be important in diseases in which the thyroid system is affected.

BRIEF DESCRIPTION OF THE DRAWINGS

FIG. 1, panels A through D show the nucleotide and predicted amino acid sequence encoded by the herbA-T clone. Open reading frames in the 5' untranslated region are underlined. The boxed sequences indicate the DNA binding domain.

FIG. 2, panels A and B show the amino acid sequence of the herbA-T clone compared with amino acid sequence of other members of the nuclear receptor family, as described in Example 1.

DETAILED DESCRIPTION OF THE INVENTION

A new thyroid hormone receptor, herein termed herbA-T (or $hTR_\alpha$), which is encoded by a cDNA clone from a human testis library, has been identified. HerbA-T has been characterized as a novel thyroid receptor and as a new member of the steroid thyroid hormone receptor family.

As used herein, "herbA-T or $hTR_\alpha$", refers to a polypeptide which functions as a thyroid hormone receptor. HerbA-T comprises a polypeptide of molecular mass about 55 kD. The term herbA-T refers both to the native amino acid sequences and to modifications thereof. Minor modifications of this sequence which do not destroy its activity also fall within the definition of human herbA-T and within the definition of the protein claimed as such. HerbA-T has substantially the amino acid sequence shown in FIG. 1. Fragments of the entire sequence of FIG. 1 which retain the activity of the entire protein are included within the definition. Moreover, the recombinant herbA-T proteins of the invention have amino acid sequences corresponding substantially to those of the native proteins. It is understood that limited modifications may be made, however, without destroying the herbA-T activity, and that only a portion of the entire primary structure may be required in order to effect activity.

As is well-known in the art, proteins can exist in neutral form or in the form of basic or acid addition salts depending on their mode of preparation or environment, if in solution. HerbA-T, in particular, may be found in the form of its acid addition salts, involving the free amino groups, or its basic salts, formed with free carboxyls. Additionally, the protein may be modified by the presence of certain biological materials such as lipids and saccharides, by side chain modifications such as the acetylation of amino groups, phosphorylation of hydroxyl side groups or oxidation or reduction of sulfhydryl groups. Included within the definition of herbA-T herein are any composition of an amino acid sequence substantially similar to that of the native sequence. Moreover, the primary amino acid sequence may be modified, either deliberately, as through site directed mutagenesis, or accidentally, as through mutation of host's DNA, but still retain herbA-T activity. All such modifications or that would also include alternative splicing are also included in the definition of herbA-T, as long as the herbA-T activity is retained.

"HerbA-T activity" as used herein, denotes the ability to bind thyroid hormone $T_3$ and/or to regulate thyroid hormone responsive, genes.

"Substantially pure," when used to describe the state of herbA-T of the invention, denotes herbA-T essentially free of other proteins or materials normally associated with or occurring with herbA-T in its native environment.

The term "DNA sequence which codes for herbA-T" as used herein refers to the primary nucleotide sequence of a gene encoding the amino acid sequence herbA-T, as defined above. An example is the sequence presented in FIG. 1. The gene may or may not be expressed in the native host. If it is not expressed in the native host, it may still be capable of being manipulated through recombinant techniques to effect expression in a foreign host. The term refers both to the precise nucleotide sequence of a gene found in a mammalian host as well as modified genes which still code for an herbA-T polypeptide having biological activity. The gene may exist as a single contiguous sequence or may, because of intervening sequences and the like, exist as two or more discontinuous sequences, which are nonetheless transcribed in vivo to ultimately effect the biosynthesis of a protein substantially equivalent to that defined as herbA-T, above. Such modifications may be deliberate, resulting from, for example, site directed mutations. Such modifications may be neutral, in which case they result in redundant codons specifying the native amino acid sequence or in such modifications which may in fact result in a change in amino acid sequence which has either no effect, or only an insignificant effect on herbA-T activity. Such modifications may include point mutations, deletions or insertions.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence coding for herbA-T" may thus refer to one or more genes within a particular individual. Moreover, certain differences in nucleotide sequences may exist between individual organisms, which are called aleles. Such allelic differences may or may not result in differences in amino acid sequence of the encoded polypeptide which still encoding a protein with herbA-T activity.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

"Expression vector" includes vectors which are capable of expressing DNA sequences contained therein, where such sequences are operationally linked to other sequences capable of effecting their expression. It is implied, although not always explicitly stated, that these expression vectors must be replicable in the host organisms either as episomes or as an integral part of the chromosomal DNA. Clearly a lack of replicability would render them effectively inoperable. In sum, "expression vector" is given a functional definition, and any DNA sequence which is capable of effecting expression of a specified DNA code disposed therein is included in this term as it is applied to the specified sequence. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

To isolate further members of the herbA gene family, a 600-bp AVA I-Pst I DNA fragment from v-herbA (viral herbA, as described in Debuire et al., Science 224:1456 (1984), which is incorporated herein by reference, encoding the cysteine-rich domains was used to screen human complementary DNA (cDNA) libraries. Two cDNA clones, which hybridized strongly with the $^{32}$P-labeled v-herbA probe, were isolated from a testis library. Both clones also hybridized with a probe from the 3' end of v-herbA. Two Eco RI inserts of the larger of these clones (herbA-T-1) were subcloned and sequenced. The 2112-bp long sequence of herbA-T-1 contains a long open reading frame of 490 amino acids with an initiator methionine codon at nucleotide 334 and a terminator codon at nucleotide 1924, as shown in FIG. 1.

Figure 1A:
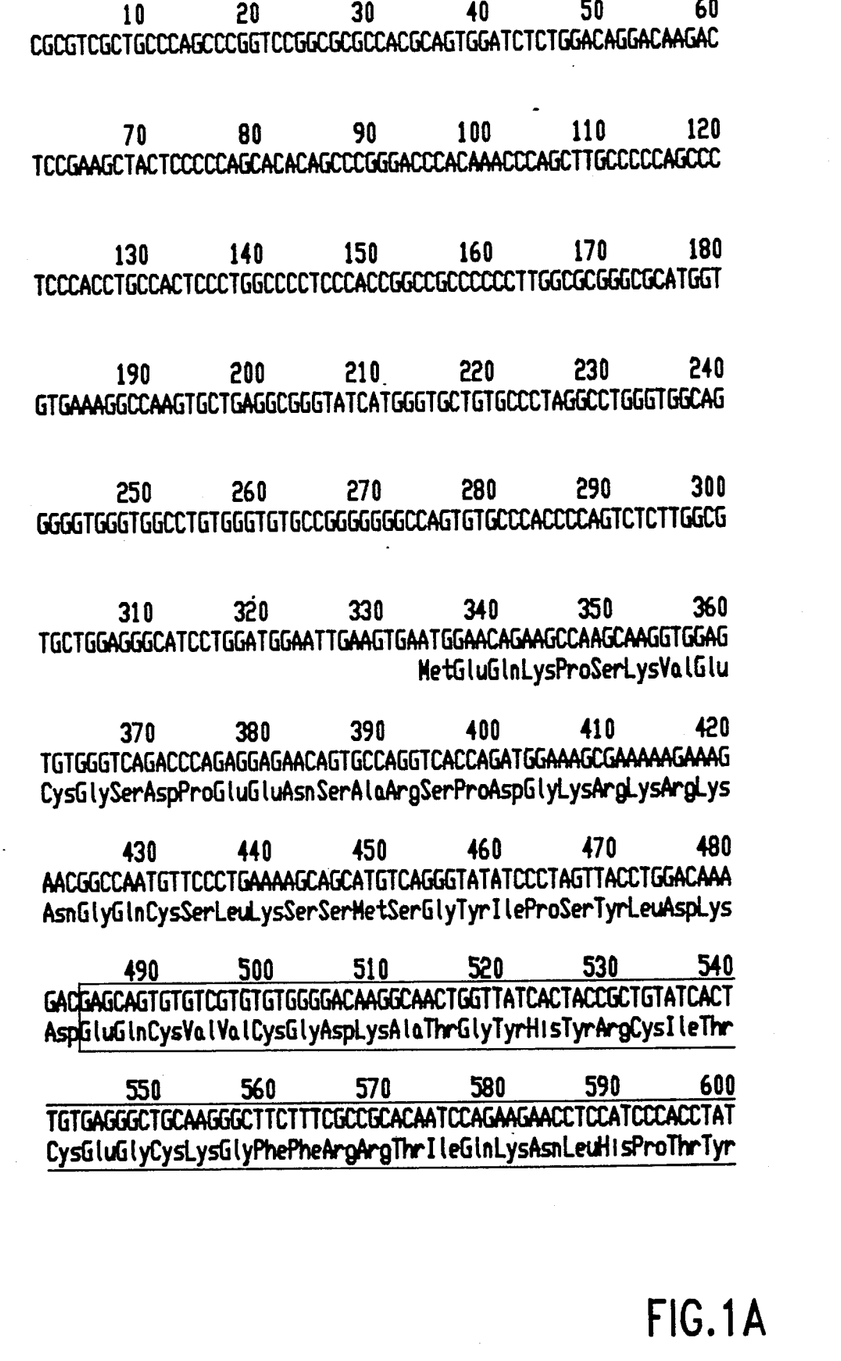
Figure 1B:
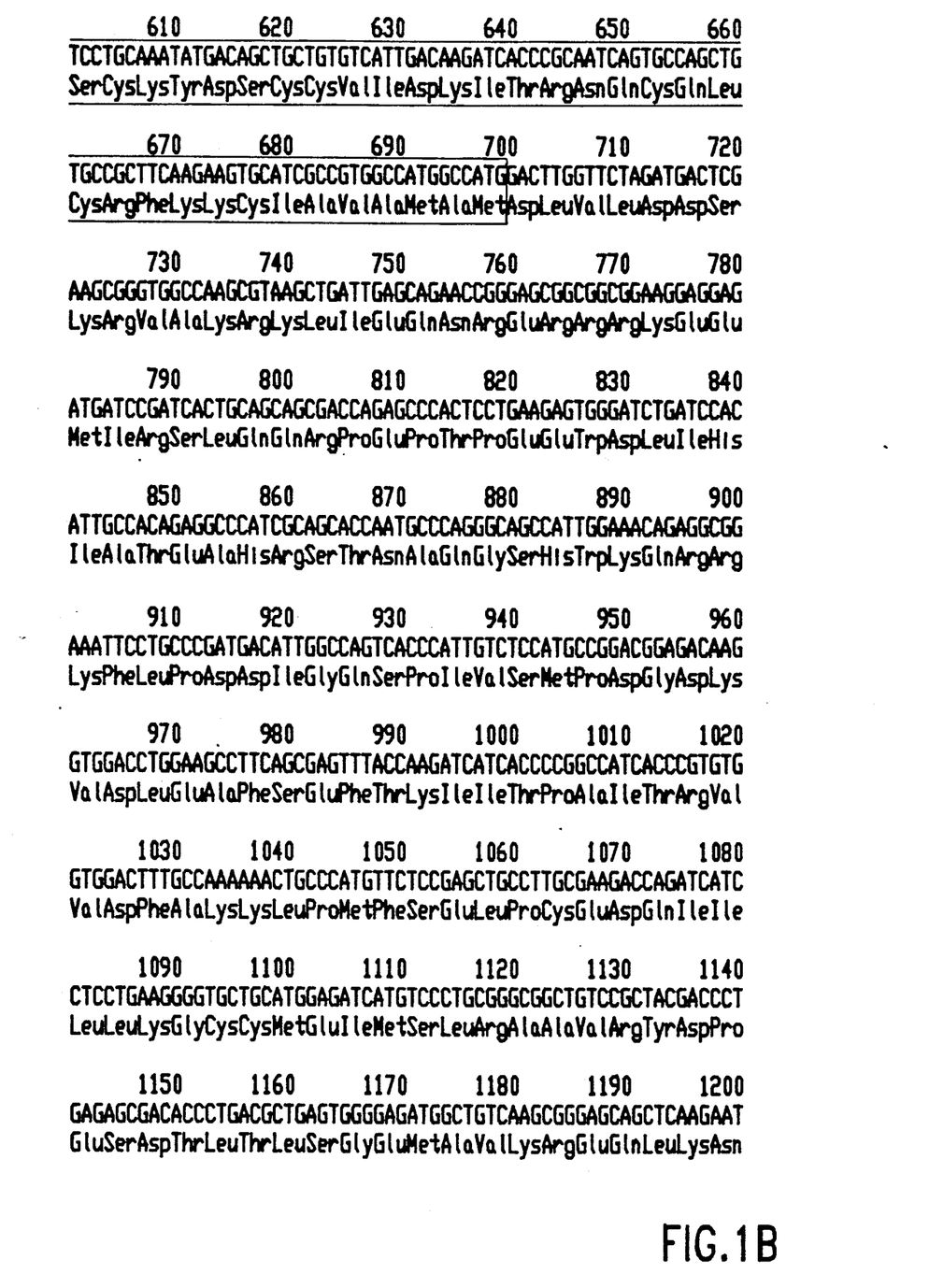
Figure 1D:
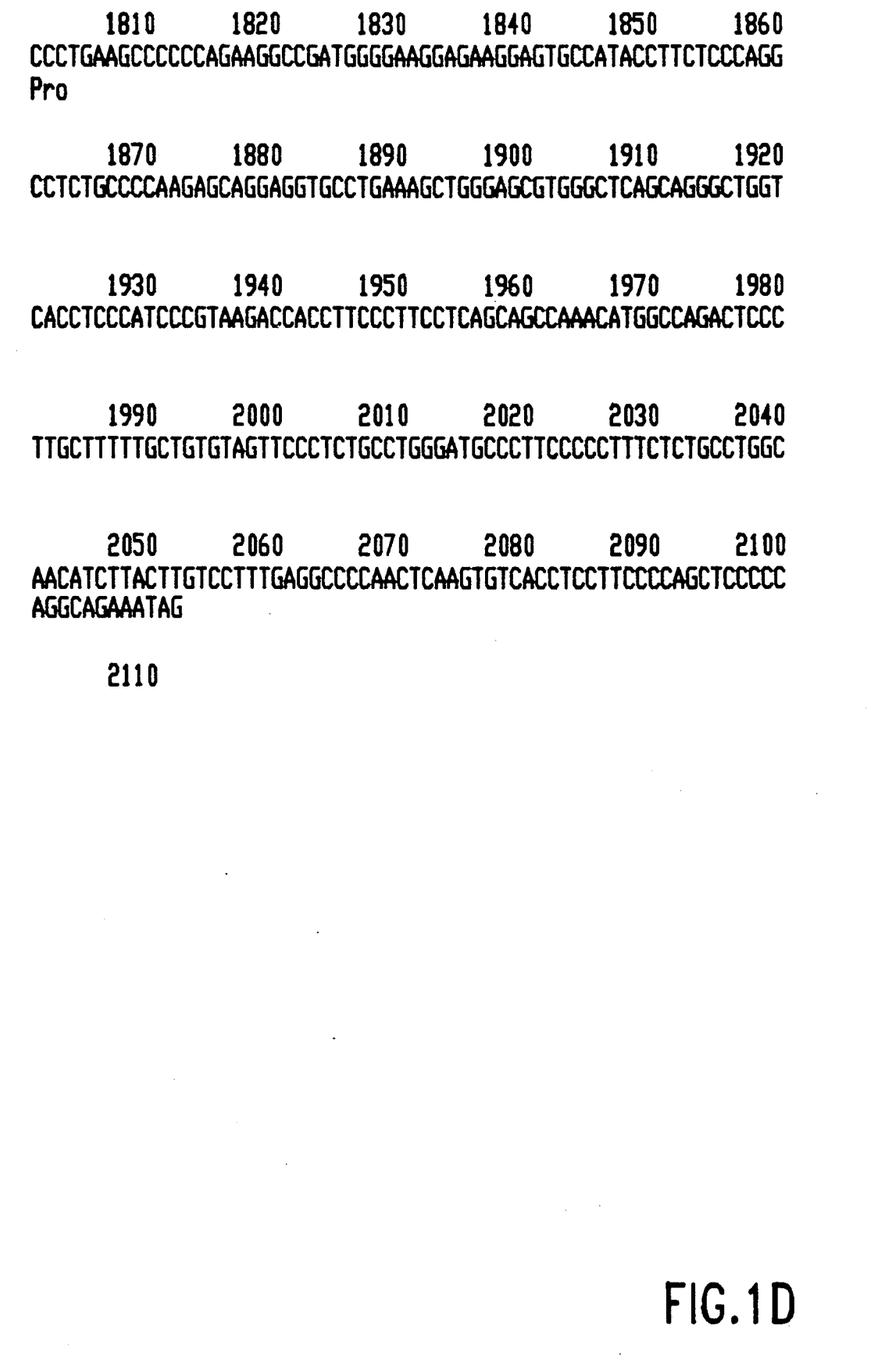
Figure 2A:
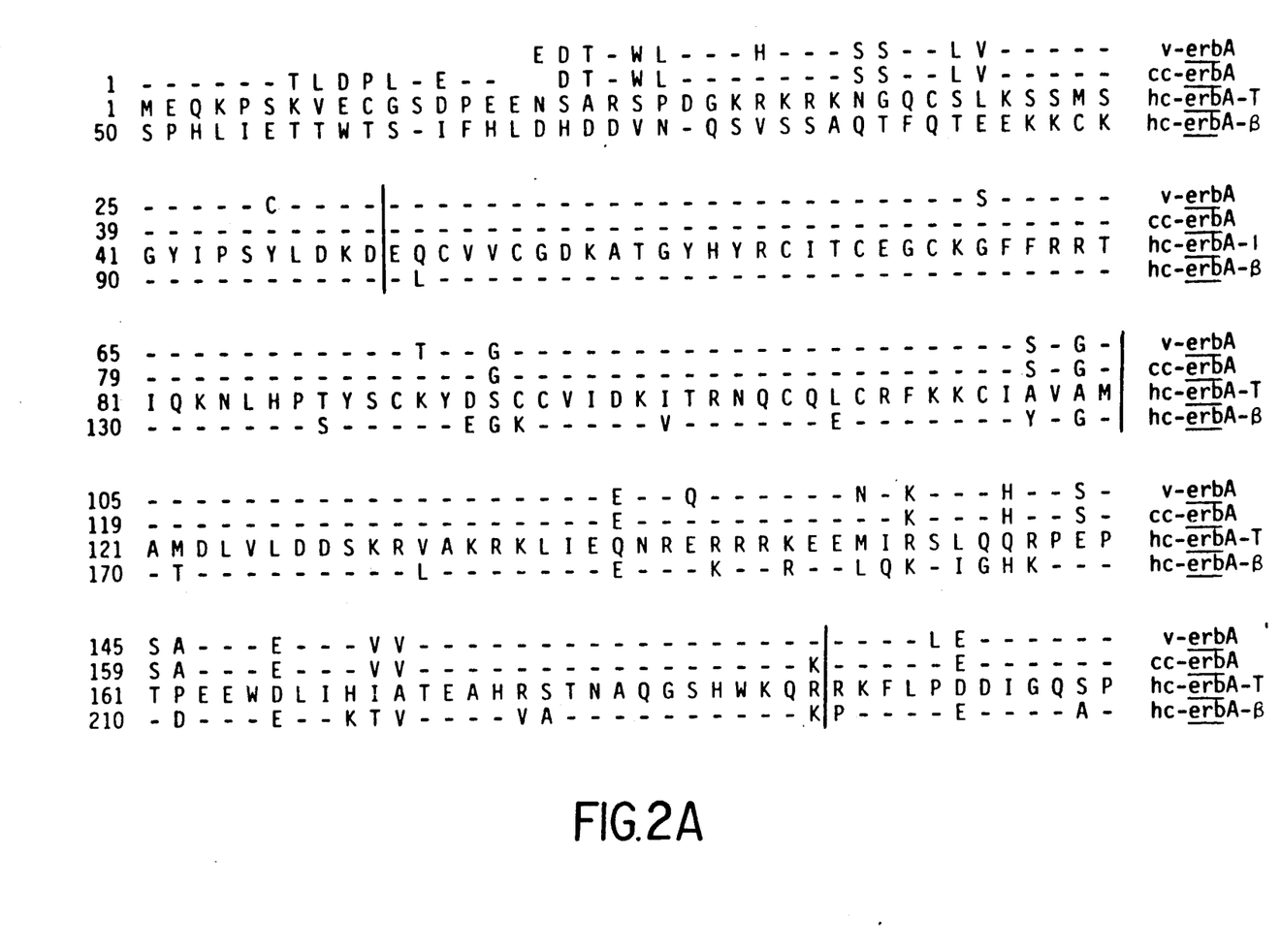
Figure 2B:
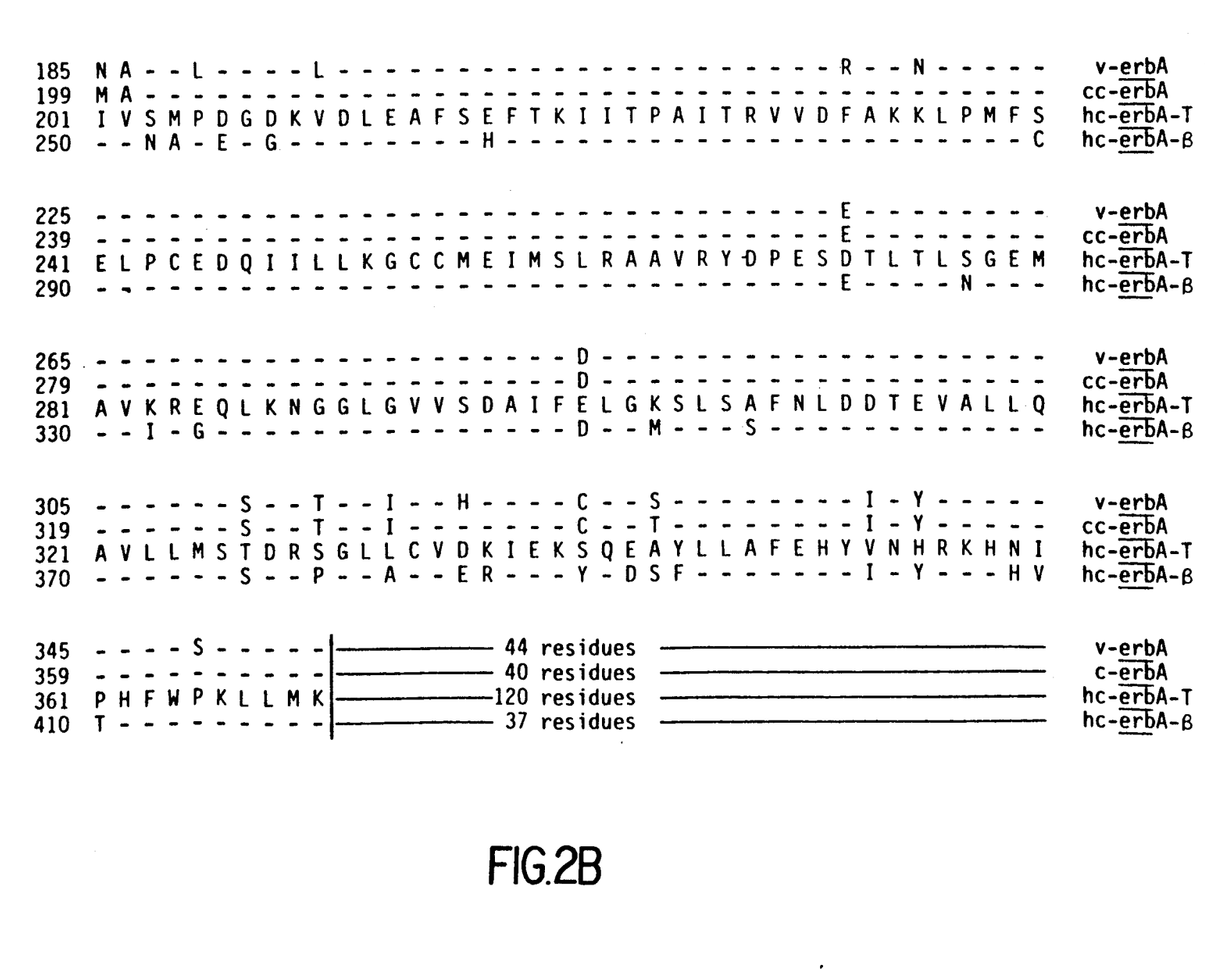
Figure 3:
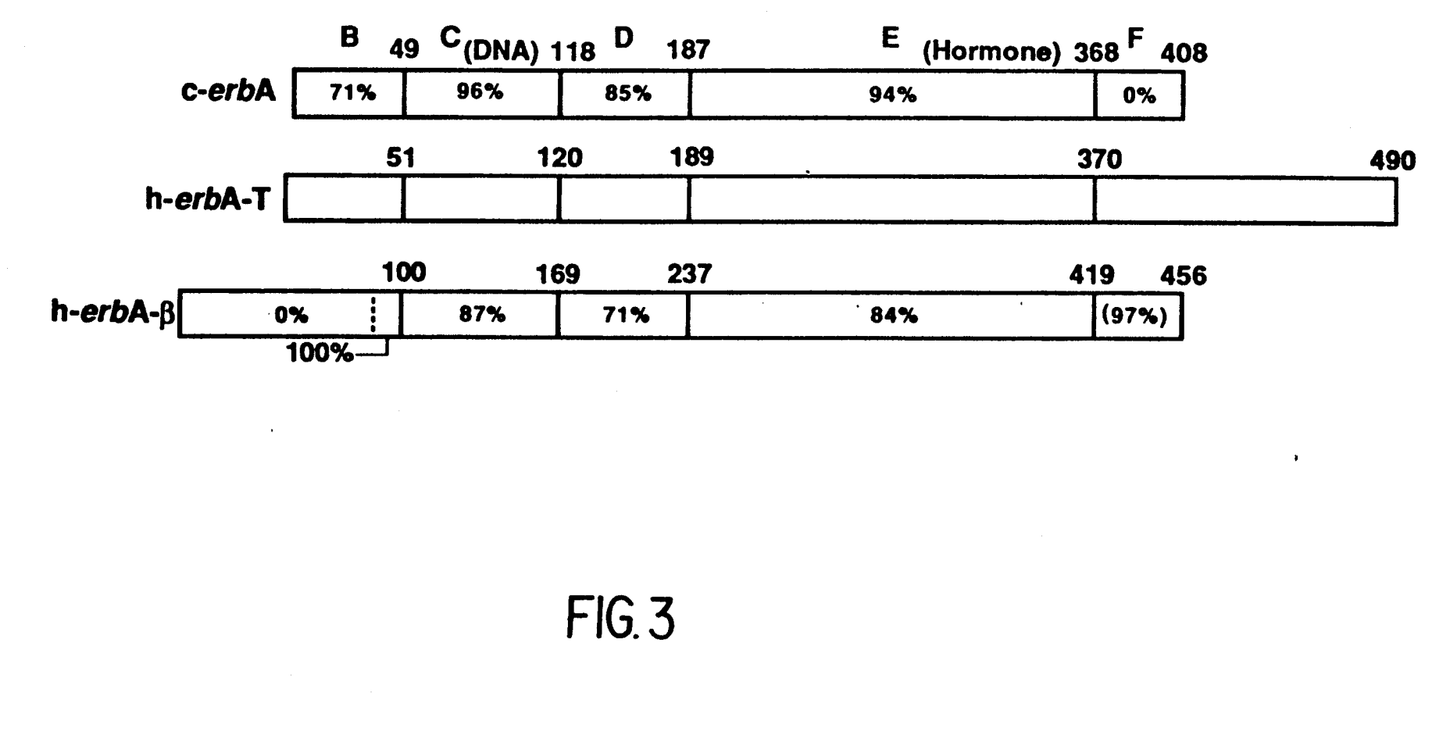
FIG. 3 shows a schematic representation of homologies between three cellular herbA proteins and the viral herbA protein.

The predicted polypeptide encoded in the herbA-T-1 clone, as shown in FIG. 1, has a molecular mass of 54,753 ($M_r$ 55,000), is larger than the polypeptides encoded by the cc-herbA and the hc-herbA-beta clones, (Sap et al., supra: Weinberger, et al., supra) but shows homology with both these proteins and the v-herbA oncogene product (FIGS. 2 and 3). The protein also contains the domains typical for steroid and thyroid hormone receptors (FIG. 3).

The human herbA-T protein is only 71% homologous with chicken herbA in the amino terminal domain and shows no homology in most of this region with human herbA-beta; the presumed DNA-binding domain is 96% homologous to the chicken protein and 87% homologous to the other human protein, respectively (FIG. 3). Domain D shows decreased homology (85% with the chicken and 71% with the other human receptor) in comparison with its adjacent domains with known functions. The carboxyl-terminal portion of the herbA-T protein shows no similarity to the other two herbA proteins. The substantial differences between the nucleotide and amino acid sequences of herbA-T and the previously known herbA proteins (FIGS. 2 and 3) show that herbA-T is a distinct protein.

Figure 4:
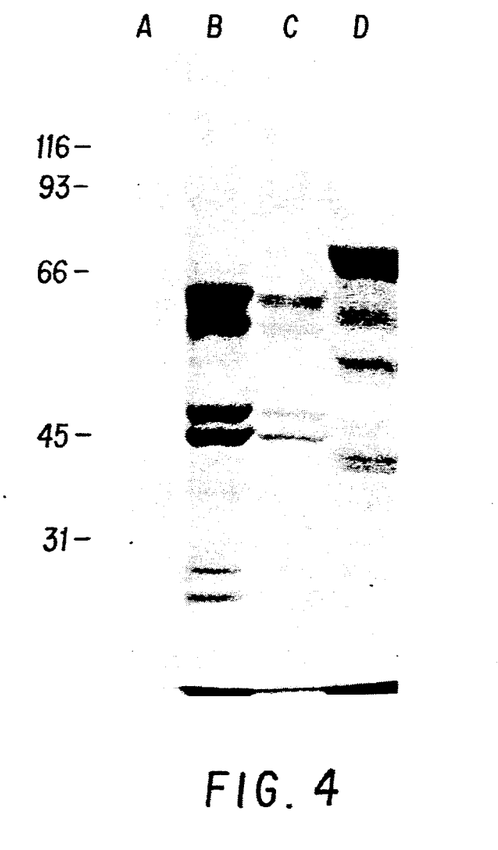
FIG. 4 shows an analysis of vitro-synthesized herbA-T protein, as described in Example 2.

The chicken c-herbA and the human c-herbA-beta gene encode high-affinity receptors for the thyroid hormone 3,5,3'-triiodo-L-thyronine ($T_3$). Because of the possibility that the new herbA-T gene product would also be a thyroid hormone receptor, in vitro transcription and translation systems were used to synthesize the protein encoded by the herbA-T clone to be able to test its affinity for thyroid hormone in vitro. As a control, the cDNA of the human estrogen receptor was used. RNA from herbA-T clones containing the complete or a partially deleted 5' flanking region was poorly translated (FIG. 4), whereas RNA from a clone (T-1-4) in which we deleted all but 37 bp of the 333-bp 5' flanking region was translated as efficiently as the estrogen receptor control RNA (FIG. 4). Four major protein bands were detected when the T-1-4 clone was transcribed in the sense direction and translated. The largest protein (about $M_r$ 56,000) probably represents the complete polypeptide encoded in the herbA-T clone. The smaller proteins may represent translation products initiating at internal AUG codons, or they could be products of incomplete translation or proteolytic breakdown.

To measure specific hormone binding to the translation products, $^{125}$I-labeled $T_3$ was added to the translation reactions in the presence and absence of a 1000-fold excess of unlabeled hormone, the estrogen receptor translation product serving as one control. As further control, untreated reticulocyte lysate was also incubated with $^{125}$I-labeled $T_3$ in the presence and absence of unlabeled hormone.

Figure 5:
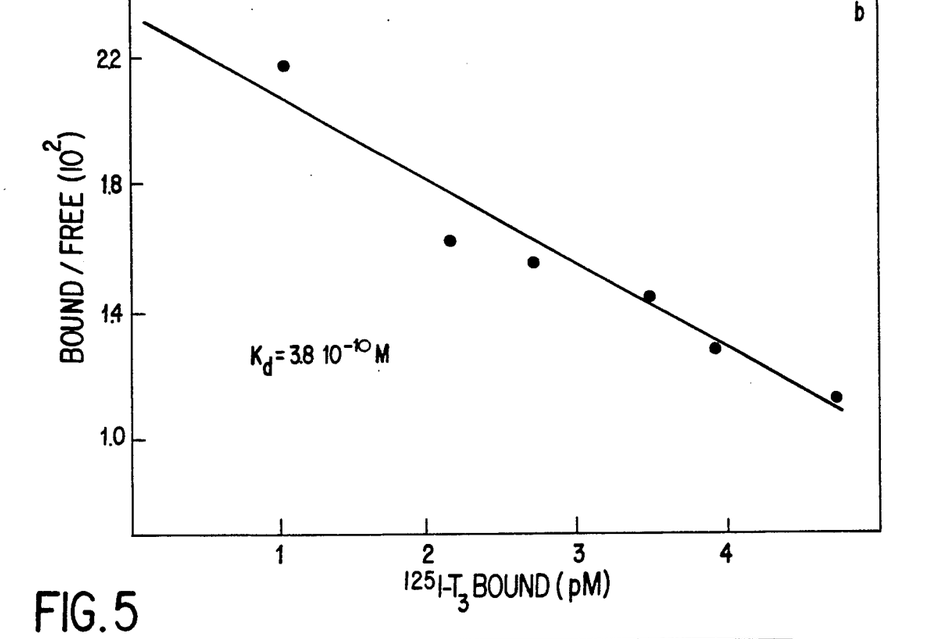
FIG. 5 shows the specific binding of thyroid hormone $T_3$ by in vitro synthesized herbA-T protein and the analysis of the affinity of this interaction as described in Example 3.

FIG. 5 illustrates specific $T_3$ binding by the herbA-T protein when incubated with increasing concentrations of the labeled hormone. At high concentrations of the hormone, some $T_3$ binding was also detected in the control extract. Scatchard analysis of $T_3$ binding revealed a dissociation constant ($K_d$) of $3.8 \pm 0.2 \times 10^{10}$ M.

The existence of multiple thyroid hormone receptors allows the assumption that these different receptors fulfill different functions in that they are either tissue-specific, have different ligand affinities, or are able to activate different genes.

Nucleic acid probes and antibodies specific for herbA-T can be used to assess the expression of this receptor in tissues for diagnostic purposes. Nucleic acid probes suitable for such analyses can be prepared from the herbA-T clone or by synthesizing oligonucleotides duplicating herbA-T sequences from regions where this sequence differs from the other members of the family so as to hybridize only with the homologous sequence under stringent conditions. The oligonucleotides can be used as such to detect the herbA-T encoding mRNA or they can be used to isolate herbA-T cDNA clones from libraries. The probe can be labelled, using labels and methods well known in the art.

Antibodies to the receptor are generated by immunizing with the receptor protein or its fragments isolated from natural sources or produced from the cDNA in a bacterial or eukaryotic expression system by using methods well known in the art. Alternatively, antigenic peptides can be synthesized by chemical methods well known in the art.

The herbA-T protein can be used to produce either polyclonal or monoclonal antibodies. If polyclonal antibodies are desired, purified herbA-T protein, or antigenic fragments thereof, is used to immunize a selected mammal (e.g. mouse, rabbit, goat, horse, etc.) and serum from the immunized animal is later collected and treated according to known procedures. Antisera containing polyclonal antibodies to a variety of antigens in addition to the herbA-T protein can be made substantially free of antibodies which are not anti-herbA-T specific by passing the composition through a column to which non-herbA-T proteins prepared from the same expression system without herbA-T have been bound. After washing, antibodies to the non-herbA-T proteins will bind to the column, whereas anti-herbA-T antibodies elute in the flow through. Such methods are well known.

Monoclonal anti-herbA-T antibodies can also be readily produced by one skilled in the art. The general methodology for making monoclonal antibodies by fusing myelomas and lymphocytes to form hybridomas is well known. Such cells are screened to determine whether they secrete the desired antibodies, and can then be grown either in culture or in the peritoneal cavity of a mammal. Antibodies that can be antibody producing cell lines can also be created by techniques other than fusion, such as direct transformation of B lymphocytes with oncogenic DNA, or transfection with Epstein-Barr virus, See, e.q., M. Schreier et al., HYBRIDOMA TECHNIQUES (1980); Hammerling et al., MONOCLONAL ANTIBODIES AND T-CELL HYBRIDOMAS (1981); Kennett et al., MONOCLONAL ANTIBODIES (1980), which are incorporated herein by reference.

Antibodies specific to herbA-T have a number of uses. For example, they may be employed in an immunoassay to detect the presence of herbA-T. Various appropriate immunoassay formats are well known to those skilled in the art. See for example HANDBOOK OF EXPERIMENTAL IMMUNOLOGY, (D.M. Weir, Ed.) Blackwell Scientific Publications (3rd ed. 1978), which is incorporated herein by reference.

Moreover, since this thyroid receptor is a human homologue of the viral oncogene herbA, tumor growth can be affected by the level of this receptor. Measurement of the receptor or its RNA will help assess this. These determinations can be made at the RNA level with nucleic probes and at the protein level with antibodies. Finally, the receptor and its cDNA are useful in the identification of optimal agonist and antagonists of the receptor for therapeutic use.

Agonists and antagonists specific for the herbA-T thyroid hormone receptor can be used to activate tissue specific thyroid hormone receptor and thereby provide means to develop tissue specific thyroid hormone therapies for certain diseases and cancers. To identify agonists and antagonists of the receptor, a hybrid receptor consisting of the DNA binding domain of the estrogen receptor and the hormone binding domain of the thyroid hormone receptor is constructed. This receptor can be used in a cotransfection experiment as described by Benbrook et al. Nature 333:669 (1988) with and estrogen responsive indicator gene. To determine the biological activity of thyroid hormone derivatives, these compounds are added to the transfected cells which are harvested subsequently to determine the indicator gene activity. Agonists result in an increased activity of the indicator gene; antagonists prevent the action of agonists in this assay.

The following examples are intended to illustrate but not limit the invention.

EXAMPLE I

Cloning and sequencing of herbA-T cDNA

Human testis cDNA lambda gt$_{11}$ library (J. L. Millan, C. E. Driscoll, K. M. LeVan, E. Goldbert, *Proc. Natl. Acad. Sci. USA* 84:5311 (1987), which is incorporated herein by reference) was used as the source of the cDNA. Approximately $3 \times 10^5$ plaques were screened with a 32P-labeled probe obtained from a randomly primed and transcribed (A. P. Feinberg and B. Vogelstein, *Anal. Biochem.* 137:266 (1984) which is incorporated herein by reference) 600-bp Ava I-Pst I fragment from v-herbA encoding the cysteine-rich domain. Hybridization was performed under high stringency conditions at 55° C. 5×saline, sodium phosphate, and EDTA (SSPE) (1 × SSPE=0.18M NaCl, 0.0M NaPO$_4$, pH7.7, 0.01M EDTA), 1 × Denhardt's solution, 5% Dextran sulfate, and salmon sperm DNA (100 ng/ml) followed by two 15-minute washes in 2×standard saline citrate, 0.1% SDS (1×standard saline or rate=0.15M NaCl, 0.15M sodium citrate) at room temperature, then two 60-minute washes in 5 ml SSPE, 1×Denhardt's 0.1%

SDS at room temperature. For DNA sequencing, the Eco RI inserts from the lambda gt$_{11}$ clone, herbA-T-1, were cloned into the EcoRI site of the sequencing vector, Bluescript (Stratagene Cloning Systems, Inc., La Jolla, CA). Sequential deletions extending from both sides into the Eco RI insert were created by means of the Exo III deletion method (S. Henikoff, Gene 28:351 (1984), which is incorporated herein by reference) the deletion clones were sequenced from double stranded DNA (E. Y. Chen and P. H. Seeburg, DNA 4:165 (1985), which is incorporated herein by reference to obtain the complete sequence from both strands. The cDNA sequence of the herbA-T-1 clone and complete amino acid sequence of the herbA-T protein encoded by it are shown in FIG. 1. FIG. 2 compares the amino acid sequences of three cellular erbA proteins and the viral erbA gene product. FIG. 3 is a schematic representation of homologies among erbA proteins. Domains were designated in accordance with Krust et al. 28 EMBO J. 5:891–897 (1986), which is incorporated herein by reference. The cysteine-rich DNA-binding domain (C) and the hormone-binding domain (E) are connected by a possible hinge region (D). Domains C and E have been defined by mutations for both the glucocorticoid and the estrogen receptor, whereas direct functions for the two terminal domains, B and F, have not yet been determined. Percent homologies between the herbA-T protein and the chicken herbA protein and human β protein are also indicated in FIG. 3. In one case, the percent homology between the human β and the chicken protein is also indicated in parentheses.

EXAMPLE II

In vitro translation of the herbA-T protein

For in vitro transcription and translation, the Bluescript sequencing vector (Stratagene Cloning Systems, La Jolla, CA) was used. This vector contains T$_7$ and T$_3$ promoters flanking the multiple cloning box. DNAs linearized at a unique restriction enzyme site in the vector cloning box at the 3' end of the insert were transcribed with T$_7$ or T$_3$ polymerase at 37° C. for 30 minutes. Transcription mixtures (25μl) contained 1μg of restricted DNA templates, 25 units of ribonuclease-block (Stratagene), 10 units of T$_3$ or T$_7$ polymerase (Stratagene) in transcription buffer (40 mM tris, pH 8, 8 mM MgCl$_2$, 2mM spermidine, 30 mM dithiothritol, and 0.4 mM of all four ribonucleotides.)

The DNA template was then digested with ribonuclease-free deoxyribonuclease I. The RNA transcripts were translated in micrococcal nuclease-treated rabbit reticulocyte lysates (Promega Biotec Madison, WI) in the presence of $^{35}$S-labeled methionine under conditions suggested by the manufacturer's instructions. No differences were detected when capped or uncapped RNAs were used. Proteins were separated on a 15% SDS-polyacrylamide gel. Lane A, lysate without RNA; lane B translation of RNA from clone T-1-4 (which has 296 bp deleted from the 5' end); lane C translation of RNA from clone T-I-222 (which has 22 bp deleted from the 5' end); lane D translation of RNA from a construct that contains the human estrogen receptor cDNA.

EXAMPLE III

Hormone Binding Assay

Proteins were synthesized in vitro essentially as described above except that instead of labelled methionine unlabeled methionine was added. Protein extracts were diluted eightfold in T$_3$ buffer (20 mM tris, pH 7.5, 10% glycerol, 50 mM NaCl, 1 mM MgCl2, 5 mM mercaptoethanol) and incubated for 1 hour at 28° C. in the presence of $^{125}$I-labeled hormone. Bound T$_3$ was determined by a filter-binding assay (A. Inoue, J. Yamakawa, M. Yakoika, S. Morisawa, Anal. Biochem. 134:176 (1983) which is incorporated herein by reference). The incubation mixtures were resuspended in 800 μl of ice-cold T$_3$ buffer and filtered over Millipore filters, type HAWP02500, and washed four times with 800 μl of cold T$_3$ buffer. Bound radioactivity was determined in a liquid scintillation counter. To determine the amount of specifically bound $^{125}$I-T$_3$, incubation mixtures were also incubated in the presence of a 1000-fold excess of unlabeled hormone over labeled hormone; as a control, reticulocyte lysate was incubated with labeled hormone and a mixture of labeled and unlabeled hormone. The assay results are shown in FIG. 5.

Figure 6:
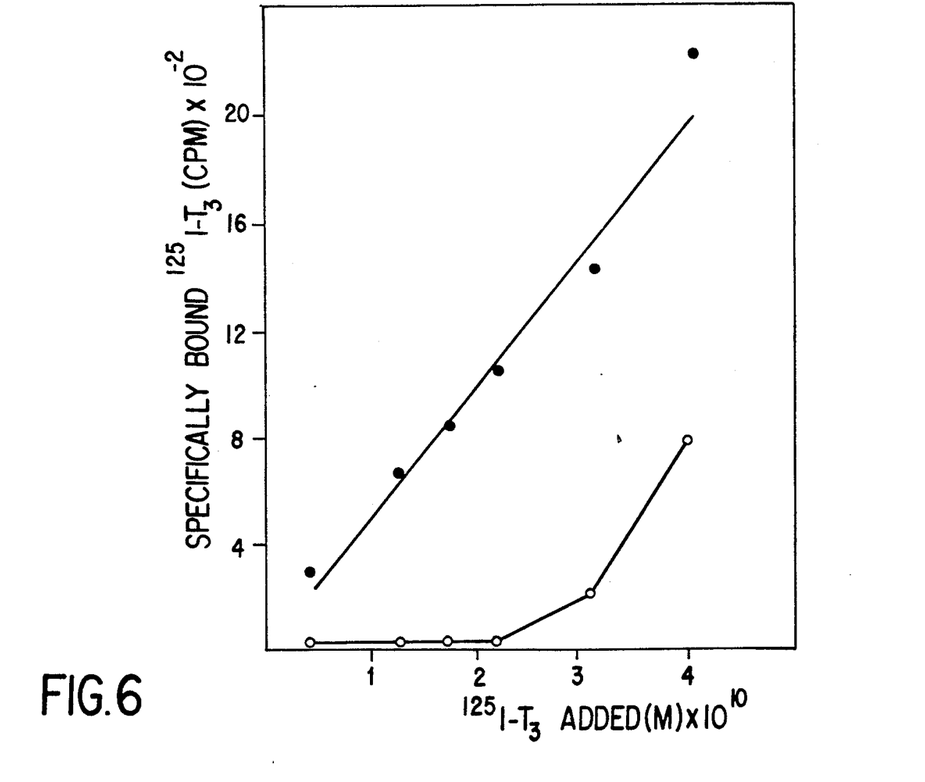
FIG. 6 shows a Scatchard plot of binding.

In vitro translated protein from clone T-1-4 was incubated with various concentrations of 125I-T$_3$ (New England Nuclear Boston, MA) in the presence and absence of unlabeled T$_3$. Specifically bound radioactivity (radioactivity bound in the absence of unlabeled T$_3$ minus radioactivity bound in the presence of an excess of T$_3$) were determined as described above (filled circles). Specific binding to reticulocyte lysate which had not been incubated with RNA is also shown open circles. Scatchard plot binding data are shown in FIG. 6 (Scatchard, Ann NY Acad Sci 51:660 (1949), which is incorporated herein by reference. For these calculations, the radioactivity bound (expressed in counts per minute) in the control extract were subtracted from the specifically bound radioactivity in the T-1-4 extract.

EXAMPLE IV

IDENTIFICATION OF AGONISTS AND ANTAGONISTS

Agonists and antagonists of the herbA-T receptor can be identified using a variation of the "finger-swap" approach to determine the ligand-specificity pioneered by Green and Chambon, (Nature 324:615 (1986), which is incorporated herein by reference) as modified in Benbrook et al., (Nature 333:669 (1988), which is also incorporated herein by reference). The DNA-binding domain (which presumably forms two zinc-binding fingers) of the herbA-T receptor is exchanged with the DNA-binding domain of the estrogen receptor, Green et al., Nature 320:134 (1986) for which specific hormone-responsive DNA elements (HRE) have been identified. The hybrid receptor is used to transfect susceptible tissue-culture cells, such as HeLa cells, together with a reporter gene containing the relevant HRE. The effect of various potential agonists of the unknown receptor can then be measured from cells transfected with both genes and grown in the presence and absence of the various ligands. The presence of CAT can be monitored by the standard assay, Gorman et al., Molec. Cell Biol. 2:1044 (1982), which is incorporated herein by reference.

T$_3$ will induce CAT gene expression at physiological concentrations. In addition, herbA-T agonists can be identified using such co-transfected cells. Material suspected of functioning as an agonist is added to the cell culture. CAT expression indicates that the material is agonistic. Conversely, the cessation of CAT expression in the activated system upon the addition of a material indicates that the material functions as an antagonist.

Although the invention has been described with reference to the presently-preferred embodiment, it should be understood that various modifications can be made without departing from the spirit of the invention. Accordingly, the invention is limited only by the following claims.

I claim:

1. A substantially purified polypeptide having a sequence consisting essentially of the amino acids shown in FIG. 1 for herbA-T.
2. An antibody specifically reactive with herbA-T protein as defined in claim 1.
3. The antibody of claim 2 wherein said antibody is monoclonal.
4. The antibody of claim 2 wherein said antibody is polyclonal.

* * * * *